United States Patent
Harrel

(10) Patent No.: US 6,726,531 B1
(45) Date of Patent: Apr. 27, 2004

(54) ABRASIVE TOOL HAVING SAFE AND ACTIVE AREAS

(76) Inventor: Stephen K. Harrel, 4510 Ridge Rd., Dallas, TX (US) 75229

( * ) Notice: Subject to any disclaimer, the term of this patent is extended or adjusted under 35 U.S.C. 154(b) by 0 days.

(21) Appl. No.: 09/534,924

(22) Filed: Mar. 23, 2000

Related U.S. Application Data

(60) Provisional application No. 60/126,474, filed on Mar. 26, 1999.

(51) Int. Cl.$^7$ ................................................. B24B 1/00
(52) U.S. Cl. ........................ 451/28; 451/54; 451/165; 451/910; 433/119; 433/125
(58) Field of Search ................. 451/165, 552, 451/553, 555, 557, 558, 910, 54, 55, 28; 433/119, 165, 166, 125

(56) References Cited

U.S. PATENT DOCUMENTS

| | | | |
|---|---|---|---|
| 555,974 A | * | 3/1896 | Roberts et al. |
| 2,694,885 A | | 11/1954 | Peden |
| 2,797,535 A | | 7/1957 | Atkinson |
| 4,110,908 A | * | 9/1978 | Cranston ........................ 32/50 |
| 4,283,175 A | | 8/1981 | Nash ........................... 433/119 |
| 4,353,696 A | * | 10/1982 | Bridges ....................... 433/125 |
| 4,389,192 A | * | 6/1983 | Neuwirth ..................... 433/166 |
| 4,634,379 A | * | 1/1987 | Nash ........................... 433/166 |
| 4,677,962 A | | 7/1987 | Loos et al. ............. 125/11 CD |
| 4,684,346 A | * | 8/1987 | Martin ........................ 433/166 |
| 4,731,019 A | | 3/1988 | Martin ........................ 433/119 |
| 4,785,586 A | * | 11/1988 | Kratfel |
| 5,797,744 A | * | 8/1998 | Rosenberg ................... 433/166 |

* cited by examiner

*Primary Examiner*—Eileen P. Morgan
(74) *Attorney, Agent, or Firm*—Chauza & Handley, LLP; Roger N. Chauza

(57) ABSTRACT

A tool for abrading a workpiece to smooth the surface thereof. In one embodiment, the tool is an ultrasonic tip (12) having plural grooves (16) formed in a smooth surface (14) thereof. Each groove (16) includes an abrasive material (24) coating the depression thereof. Rough surface areas of a workpiece projecting into the groove (16) are abraded to thereby result in a smooth workpiece surface. Once the surface roughness of the workpiece has been removed, the smooth areas (14) of the ultrasonic tip (12) are engaged, thereby preventing further abrasion of the workpiece.

23 Claims, 2 Drawing Sheets

ABRASIVE TOOL HAVING SAFE AND ACTIVE AREAS

CROSS-REFERENCE TO RELATED APPLICATIONS

This Patent Application claims the benefit of pending Provisional Patent Application entitled "ULTRASONIC ACTIVATED SCALING TIP," filed Mar. 26, 1999, and bearing Ser. No. 60/126,474, the entire disclosure of which is incorporated herein by reference.

TECHNICAL FIELD OF THE INVENTION

The present invention relates in general to tools that are moveable on work surfaces to perform operations thereon, and more particularly to tools of the type having safe areas and active areas to remove rough surface areas and provide a smooth surface.

BACKGROUND OF THE INVENTION

Tools are utilized by many different crafts persons for working on various types of materials to fabricate an object with the desired shape or form. While the majority of tools are utilized by machinists and other crafts persons working in similar trades, various types of tools are also utilized on a daily basis by artists, carpenters, cabinet makers, engineers, physicians, dentists, etc. Depending on the application to which the tool is applied, the particular devices may be moved by hand, rotated, reciprocated or otherwise vibrated to operate upon the surface of the workpiece.

In many applications, there is a need to smooth an otherwise rough workpiece surface. Hand files, sanders, shapers, planers, etc., are well adapted for creating a smooth workpiece surface. While these and other tools are well adapted for carrying out this function, the operation of such type of tools requires a certain degree of skill to prevent an excessive amount of material from being removed from the workpiece to prepare a smooth surface. In other words, in utilizing many of these smoothing-type tools, the operator must be careful to halt the operation once the surface is smooth, otherwise, the continued operation of the equipment will only unnecessarily remove further material from the workpiece.

In the dental field, doctors routinely utilize ultrasonic scalers to remove brittle calculus, tartar, altered cementum and other accumulated residue from a patient's tooth. During supragingival scaling or root planing, the material to be removed is universally rough with multiple jagged and protruding edges. The buildup on the enamel of a tooth is undesirable which, if not removed, can be damaging to the tooth and gingival tissue. The ultrasonic scaler is equipped with a tip which mechanically vibrates at a high frequency. When brought into contact with the hardened residue, the brittle material is fractured and eroded and removed from the tooth. The end of the metal tip of the ultrasonic scaler insert fractures and breaks the brittle buildup with a micro-hammer action. This method of removing calculus from a patient's tooth is well documented in the dental literature. In order to facilitate the removal of calculus and other materials formed over time on a patient's tooth, the ultrasonic tip can be coated with diamond particles, such as disclosed in U.S. Pat. No. 4,731,019 by Martini. The diamond particles covering the ultrasonic scaler tip function to accelerate the abrasion of the brittle calculus. Indeed, an extreme amount of care must be exercised by the doctor in the utilization of this tool, otherwise, the surface of the tooth will be abraded and damaged. It can be appreciated that the doctor or assistant must be very attentive when utilizing this ultrasonic tool, otherwise, the tooth, bone or other hard surface will be damaged beyond repair. It will also be appreciated that when the tip of this tool is utilized on that part of the tooth in the gingival pocket, excessive tooth abrasion can occur because the surgeon is unable to visually observe the tooth surface being operated upon. As a result, diamond coated ultrasonic tips have been limited to a small specialty area of dentistry by experienced doctors, namely, the periodontal surgical area.

Ultrasonic operated devices utilize tips that are constructed of specified lengths so as to be tuned A tuned tip provides optimum magnitude vibrations and thus is effective to micro-hammer object surfaces. Standard ultrasonic tips are effective only along about 4–6 mm at the end of the tip to remove accretions on a tooth surface. The other portion of the ultrasonic tip is less effective as an instrument to remove calculus and tartar buildup on tooth surfaces.

It is well known in the art to bond diamond particles to tool bits, and the like, in order to accelerate abrasion of the workpiece and extend the life of the tool. Diamond whetstones are such type of tools. These tools are fabricated by bonding a diamond abrasive in raised islands on the surface of the tool. The raised islands of diamond particles are effective to erode the surface of the workpiece. Again, the surface of the workpiece continues to be eroded as long as the operator moves the whetstone over the surface of the workpiece.

As noted above, ultrasonic scaler tips that are covered with a diamond abrasive grit currently exist. Abrasive or sharp edges on the surface of a scaler tip have been shown to be an effective means of removing tartar and roughness from the tooth surface. However, studies have demonstrated that abrasive areas and sharp edges, when vibrated by an ultrasonic scaler and placed directly against the tooth surface, will damage the surfaces of the tooth and root. In other words, not only the calculus, tartar, and other unwanted rough surfaces will be removed as desired, but a significant portion of the tooth surface will also be removed, thus causing permanent damage to the tooth.

From the foregoing, it can be seen that a need exists for a tool that removes roughened areas of a workpiece surface, but once a smooth surface is achieved, further erosion of the surface does not occur, even if the tool continues to be moved over the work surface. Another need exists for a tool that can be used by a technician to smooth surfaces of workpieces without utilizing a high degree of skill. Another need exists for an ultrasonic tip which, when used on tooth surface that cannot be easily observed, does not continue to erode the surface of a tooth once a smooth surface is achieved.

SUMMARY OF THE INVENTION

In accordance with the principles and concepts of the invention, there is provided a tool with safe and active areas that overcome the disadvantages attendant with the known prior art tools. In one embodiment, there is provided a tool for removing rough areas from a workpiece until the workpiece is smooth. The tool includes a safe area which, when engaged with the workpiece, does not erode or abrade the surface of the workpiece. The tool also includes an active area formed as a depression in the safe area. The active area has formed therein an abrasive mechanism for abrading rough areas of the workpiece that protrude therein. In one feature of the invention, once the active area functions to remove the rough areas of the workpiece, it no longer engages the workpiece surface, whereupon the safe area of the tool comes into contact with the smooth workpiece and further removal of the workpiece material is prevented.

In a preferred embodiment of the invention, a scaling tip is fitted into or attached to various forms of ultrasonic transducers utilized in the removal of calculus and roughness from teeth and other hard tissues. In such ultrasonic instruments, the ultrasonic energy can be transmitted from a generator of ultrasonic energy, such as a magnetostrictive pile or a piezoelectric element, to metal scaler tips of various standard shapes to access different areas of the tooth surface. The metal scaler tips may additionally be smooth or may contain grooves or ridges to channel coolant water to the end of the scaler tip.

In accordance with the invention, a scaler tip which can be of various shapes, includes a metal tip having one or more shallow depressions on the portion of the tip that contacts the tooth surface. Within these depressions is an active surface that has formed an abrasive or cutting surface. This active surface may include either a coating of abrasive material such as diamond grit, or a sharpened edge of the metal of the scaler tip. The diamond grit or sharpened edge does not extend above the smooth safe areas of the scaler tip. By limiting the areas covered by abrasive, the scaler tip of the invention is safe for use on the tooth surface and does not excessively erode the tooth surface. The metal portion of the scaler tip that comes in contact with the tooth surface has a smooth surface and rounded edges, in the same manner as most existing scaler tips. Additionally, the smooth surface of the scaler tip will effectively protect the tooth and root surfaces from the abrasive or sharpened edges that are located in the shallow depressions formed in the smooth metal surface. However, rough uneven accretions of tartar or other roughness on the tooth surface will project into the shallow depressions and come in contact with the abrasive or sharp edges in the shallow grooves. The rough uneven material on the tooth will thus be rapidly removed by the abrasive or sharpened edges, thereby leaving a smooth surface. Thereafter, only the smooth, non-abrasive metal surface of the scaler will come in contact with the tooth surface. The overall result of this action is that a more rapid removal of accumulations and roughness from the tooth and root surfaces is achieved, as compared to conventional scaler tips, without undesirable damage to the tooth and root surfaces. Additionally, after the major portion of the accretions has been removed, the same scaler tip can be used to finish smoothing the tooth surface without damage. Again, this results in a more rapid tartar removal without damage to the tooth. Both speed and safety for the operator and the patient is achieved.

In accordance with a preferred method of the invention, when the active/passive scaler tip is brought against the tooth surface to be cleaned, the active surface bears on the protruding projections of the tartar or calculus that is to be removed. As this unwanted material is removed, the smooth rounded surface of the tooth is encountered. The smooth surface of the tooth does not extend into the shallow depressions of the ultrasonic tip and will therefore not encounter the active surfaces formed in the depressions. Rather, the only surface of the scaler tip that will touch the root surface will be the smooth polished metal of the main body of scaler tip and the rounded polished edges of the shallow depressions. These polished surfaces will then function in a manner similar to currently available (smooth surface) scaler tips and can be used to perform the final smoothing of the tooth surface without scratching or damaging.

BRIEF DESCRIPTION OF THE DRAWINGS

For a more complete understanding of the present invention and the advantages thereof, reference is now made to the following description taken in conjunction with the accompanying drawings in which further features and advantages will become apparent from the following and more particular description of the preferred and other embodiments of the invention, as illustrated in the accompanying drawings in which like reference characters generally refer to the same parts or elements throughout the views, and in which.

DETAILED DESCRIPTION OF THE INVENTION

While the tool constructed according to the invention is described below in connection with an ultrasonic tip utilized in periodontal operations, the principles and concepts can be employed on tools that are applicable for use in many other areas and trades. Also, while the operation of the ultrasonic tool described below is in conjunction with movement by way of ultrasonic vibrations, tools constructed in accordance with the invention can also be moved on the workpiece by other mechanisms, such as rotary, circular, reciprocatory, hand moved, or any other action by which one or the other of the tool or the workpiece is moved with respect to the other. Tools that vibrate at frequencies other than ultrasonic, such as vibrations in the sonic frequency range, can employ the principles and concepts of the invention.

Figure 1:
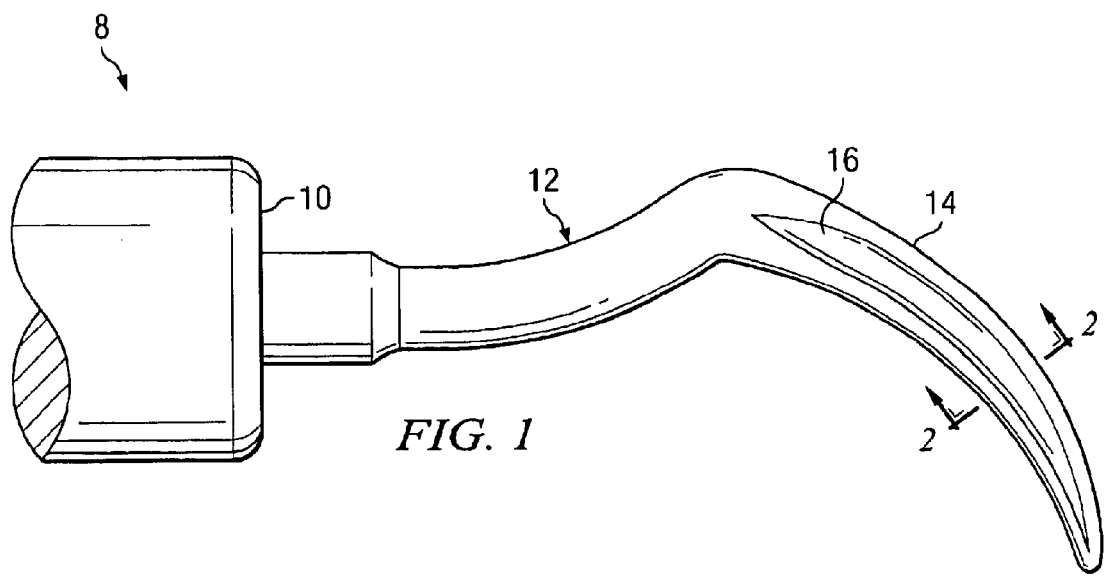
FIG. 1 illustrates an ultrasonic insert with a smooth metal scaler tip having formed therein linear depressions or grooves coated with an abrasive material.

FIG. 1 illustrates a preferred form of an ultrasonic insert 8, comprising a metal scaler tip 12 constructed similar to those that are routinely attached to ultrasonic generators for the purpose of removing roughness from the supra and sub gingival portions of a patient's teeth. Ultrasonic scaler tips 12 are typically constructed of a stainless steel or titanium material. The scaler tip 12 is mounted in a plastic holder 10 that functions as a mount for the scaler tip 12 and the ultrasonic generator or transducer (not shown). The scaler tip 12 is constructed with a smooth metal surface 14 that will not abrade or otherwise damage the surface of the tooth. Within the smooth surface 14 of the metal tip 12 are formed a number of linear depressions or grooves 16. The width and depth of the grooves are a function of the roughness of the surface material to be removed from the workpiece. For removing calculus and tartar of average buildup, the depth of each groove can be in the range of about 0.06–0.5 mm, and the width of each groove can be in the range of about 0.33–1.0 mm. The grooves are preferably milled in the hard material of the ultrasonic tip 12, but can be formed by other means. The two elongated edges of each depression 16 are rounded so as to not create a sharp edge of metal that might damage or erode the tooth surface. The edges of each groove 16 are made blunt or rounded by the use of an end mill with rounded shoulders, or by using the well-known technique of electric discharge machining. Beyond the rounded edge of smooth metal, the grooved depressions 16 are coated with an abrasive material such as diamond grit. In practice, a medium diamond grit is suitable for removing tartar and calculus from a tooth surface. The diamond grit is bonded in the depressions of the grooves 16 by standard diamond grit bonding techniques. Roughness on the tooth surface, such as tartar or calculus, will enter the depressions and be abraded by the abrasive coating. Once the tartar or calculus is removed, the abrasive coating will not come into contact with the smooth tooth surface, thereby preventing damage, wear, and abrasion of the smooth tooth surface.

Figure 2:
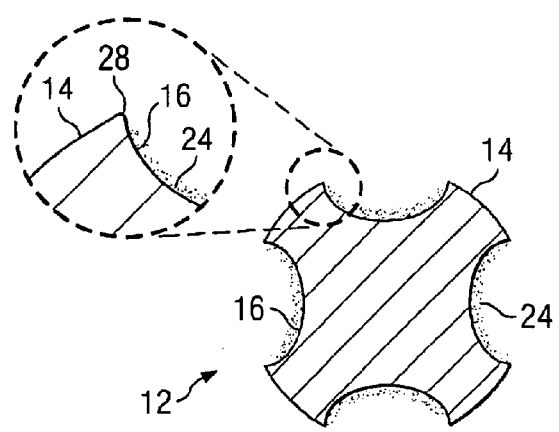
FIG. 2 is a cross-sectional view of the scaler tip of FIG. 1 taken along line 2—2, which illustrates the smooth metal surface of the scaler tip, the rounded edges of the depressions, and an abrasive coating formed on the surface of each depression.

FIG. 2 is an enlarged cross-sectional view of the scaler tip 12, taken along line 2—2 of FIG. 1. The groove depressions 16 are shown formed between the smooth metal surface portions 14 of the scaler tip 12. The rounded edges 28 of each depression 16 are shown. The edges 28 are rounded to an extent where substantially no abrasion occurs when the edges 28 contact either roughened or smooth surfaces of a tooth. The abrasive coating 24 is bonded on the trough portion of each depression 16. It should be noted that the abrasive coating 24 does not extend to the rounded edges 28 of the depression 16, thereby preventing the abrasive 24 from coming into contact with the tooth surface. The rough and protruding accretions of the calculus and tartar buildup project into the depression 16 and contact the abrasive coating 24. The rough accretions are thus rapidly removed. In practice, many more abrasive coated depressions 16 than shown can be formed around the ultrasonic scaler tip 12. Because the depth of the depressions 16 is a function of the contour of the tooth, the depressions can be formed around the ultrasonic tip 12 with different depths. Alternatively, for highly contoured tooth surfaces, a different ultrasonic tip can be employed that has depressions with smaller openings in the smooth metal surface.

Figure 3:
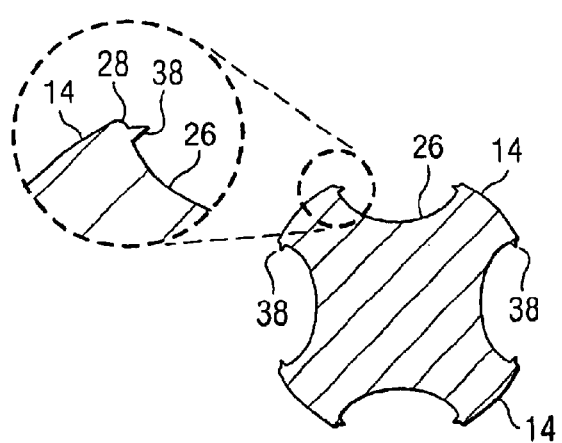
FIG. 3 is a cross-sectional view of yet another embodiment, in which the smooth metal of the scaler tip is shown with depressions therein, and with a sharpened edge of metal recessed from the smooth surface.

FIG. 3 illustrates an alternate embodiment of the scaler tip of the invention, with one portion of the scaler tip shown enlarged. In this embodiment, the depressions are shown as reference numeral 26, and are located between the smooth outer surfaces 14 of the ultrasonic scaler tip. Located below the rounded edge 28 of each depression 26 is a sharpened metal edge 38. In this embodiment, the smooth metal 14 of the scaler tip comes into contact with the tooth surface. Any tooth surface roughness, such as calculus or tartar, will come into contact with the sharpened metal edge 38 and will be rapidly removed. Those skilled in the art may also choose to coat the depressions 26 with an abrasive material to facilitate erosion of rough surfaces that project therein. The sharpened edge 38 can quickly remove tartar projections, and the abrasive coating on the depressions 26 can complete smoothing of the tooth surface.

Figure 4:
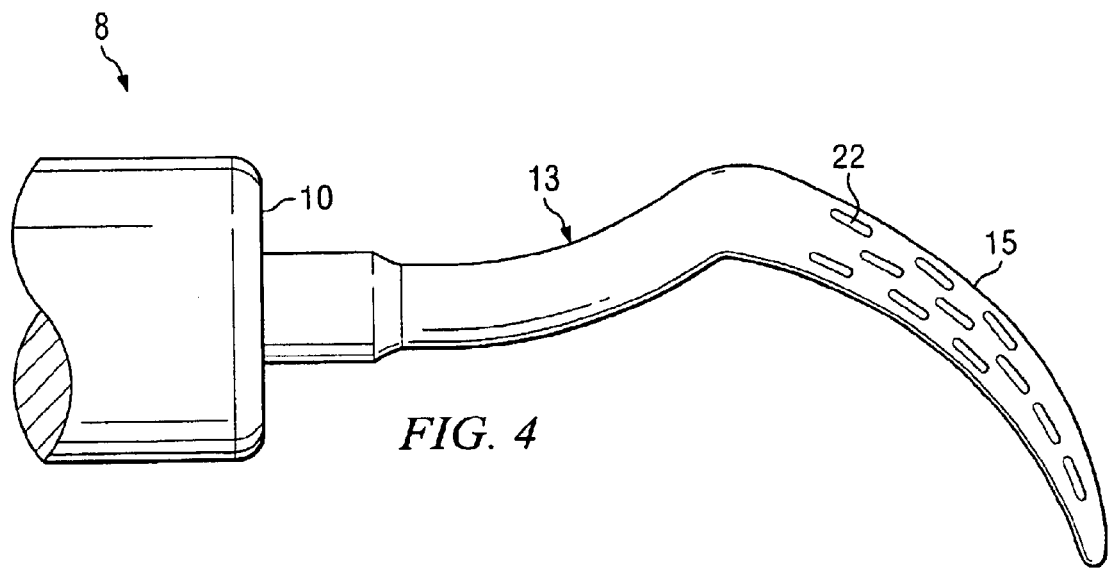
FIG. 4 illustrates another embodiment of an ultrasonic insert with a smooth metal ultrasonic scaler tip having formed therein multiple isolated depressions, each coated with an abrasive material.

FIG. 4 shows a scaler tip 13 constructed according to another embodiment of the invention. Multiple small depressions 22 are formed in the smooth metal surface of the scaler tip 13. The edges of the small depressions are again made smooth so as not to damage the tooth surface. An abrasive coating lines the depressions and functions in the same manner as described in FIG. I above. The depressions 22 are also formed and coated with an abrasive in the same manner as described above.

Figure 5:
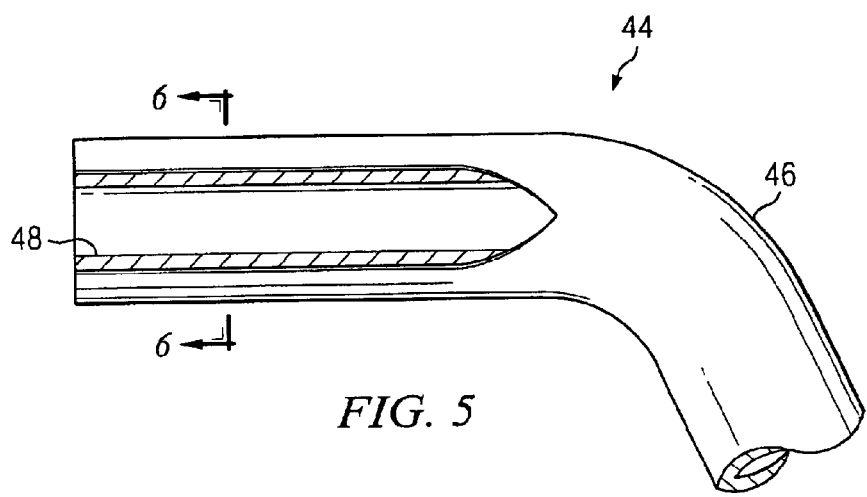
FIG. 5 illustrates a side view of yet another embodiment of the invention in which the ultrasonic scaler tip is tubular in form, with one or more windows cut therein, and where the edges of the window are smooth on the outside and sharp on the inside.
Figure 6:
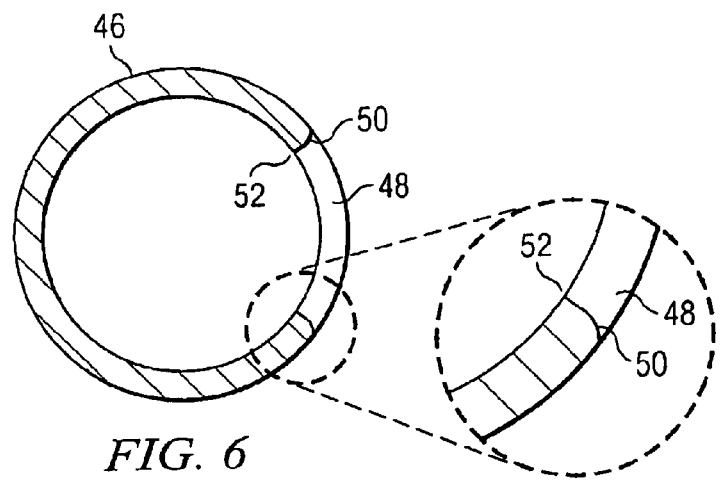
FIG. 6 is a cross-sectional view of the scaler tip of FIG. 5, taken along line 6—6 thereof

FIGS. 5 and 6 show yet another embodiment of the invention providing an ultrasonic scaler tip 44 formed as a tubular member 46. One or more windows 48 are cut into the tubular portion 46 of the scaler tip 44. The outside edge 50 of the window 48 that contacts the tooth surface is smooth and rounded so as to not cause damage or abrasion to the tooth surface. The inside edge 52 of the window 48 is sharpened in such a manner as to act on any roughness such as calculus or tartar that projects into the window 48 of the scaler tip 46. Preferably, the tubular member 46 is constructed of a rigid material, such as stainless steel or titanium, and has an outside diameter in the range of about 1–2 mm, and a sidewall thickness in the range of about 0 10–0.25 mm. The window 48 can have an arcuate opening in the sidewall the size of about 6–10 degrees, or other suitable size to accommodate the surface roughness and contour of the workpiece. The arcuate opening of the window 48 has a size that is also a function of the curvature of the workpiece. To that end, the tubular member 46 can have different size windows 48 formed therearound to accommodate different workpiece surface shapes.

In the foregoing description of the various embodiments, the smooth surfaces of the scaler tip that are not effective to substantially abrade the tooth are considered as "safe" areas, whereas the abrasive-coated areas and the sharp abrading edges are considered as "active" areas. When utilized with ultrasonic devices, the tool can be vibrated in both the subsonic and ultrasonic frequency ranges. Also, while a diamond grit abrasive is utilized in the preferred form of the invention, other grits, such as corundum and others can be utilized with suitable effectiveness.

Other combinations of the foregoing features will be evident to those skilled in the art. Many forms of smooth metal scaler tips containing depressions with active cutting or abrading elements can be used. In all of these embodiments, the principle is to allow the smooth metal surface of the scaler tip to come in contact with the workpiece, while rough accretions on the workpiece surface are acted upon by the active cutting or abrading elements. The combination of these features will rapidly remove the rough accretions from the workpiece surface while preventing damage after the removal of the accretions by only allowing the smooth metal surface to contact the workpiece. Indeed, those skilled in the art could use many depressions aligned around the tool. In practice, it has been found that the tool of the invention can be operated at a low power level, as compared to corresponding prior art tools.

While the preferred embodiment of the method and apparatus has been disclosed with reference to specific ultrasonic tips, it is to be understood that many changes in detail may be made as a matter of engineering choices without departing from the scope of the invention as defined by the appended claims. Indeed, those skilled in the art may prefer to embody the apparatus in other forms, and in light of the present description they will find it easy to implement that choice. Also, it is not necessary to adopt all of the various advantageous features of the present disclosure into a single composite tool in order to realize the individual advantage.

What is claimed is:

1. A tool for abrading raised portions from a workpiece in response to relative movement between said tool and the workpiece, comprising:
   an ultrasonic tip defining said tool
   a rigid and nonpliable material from which said ultrasonic tip is constructed;
   a working area of said ultrasonic tip adapted for engaging the workpiece, said working area having a safe area and an active area;
   the safe area of said ultrasonic tip defined by at least two spaced apart surface regions, each said surface region being a nonabrasive surface of said working area adapted for preventing abrasion of the workpiece when engaged therewith; and
   the active area including one or more depressions formed in said ultrasonic tip below a line tangent to the nonabrasive surfaces of said spaced apart regions so that said active area does not project above the nonabrasive surface of said safe area, each said depression of said active area having a size such that said workpiece will not fit therein but in which the raised portions of the workpiece will fit therein, said active area having a mechanism formed therein for abrading the raised portions of the workpiece that project into the active area, whereby when the raised portions of the workpiece are abraded, the safe area of said working area is then caused to engage said workpiece and further abrasion of the workpiece does not occur.

2. The tool of claim 1, wherein said depressions are formed with a size selected so at least a portion of said raised portions can enter into said depressions.

3. The tool of claim 1, wherein said active area comprises said depressions coated with an abrasive material.

4. The tool of claim 1, wherein said active area comprises a sharp edge formed within said depression.

5. The tool of claim 1, wherein said active abrading areas of said tool comprise one or more grooves.

6. The tool of claim 5, wherein each said groove has a depth that is a function of the height of the raised portions of the workpiece.

7. The tool of claim 1, wherein each said depression comprises a trough portion and a rounded edge joining said trough portion to said safe area, at least a portion of said trough portion being lined with an abrasive grit.

8. The tool of claim 1, wherein each said depression comprises a trough portion and a rounded edge joining said trough portion to said safe area, and further including a sharp abrading edge formed within said trough portion.

9. The tool of claim 1, wherein said depressions are formed as a plurality of grooves, each said groove extending axially along a shank portion of said tool, and each said groove spaced annularly from an adjacent groove around the shank portion of said tool.

10. The tool of claim 1, wherein said tool is constructed of a tubular member having one or more openings, each opening defined by a hole formed through a sidewall of said tubular member, said tubular member having an inner surface and an outer surface, and each said opening including a peripheral edge, and an inside edge is formed where said peripheral edge joins said inner surface, and an outside edge is formed where said peripheral edge joins said outer surface of said tubular member, and wherein said active area comprises a sharp portion of said inside edge.

11. The tool of claim 10, wherein said outside edge is structured so as to be nonabrasive.

12. The tool of claim 1, wherein said tool is structured to remove the raised portions of the workpiece without rotation of said tool.

13. The tool of claim 1, wherein the depression is constructed with a depth such that the mechanism for abrading the raised portions causes substantially complete removal of said raised portions from the workpiece.

14. A method of engaging an ultrasonic tip with a tooth surface to remove at least a portion of accretions from the tooth surface without damaging the surface of the tooth, comprising the steps of:
   using said ultrasonic tip having a working area including a safe nonabrasive area and an active abrasive area, said active abrasive area defined by at least one depression structured for abrading material, said depression surrounded by said safe nonabrasive area;
   engaging the working area of said ultrasonic tip with the section of the tooth surface having said accretions;
   moving the working area of said ultrasonic tip in contact with the tooth surface so that the accretions of the tooth surface project into said active abrasive area and at least a portion of the accretions are removed;
   continuing movement of the working area of said ultrasonic tip on the tooth surface to remove portions of the accretions; and
   wherein after at least a portion of the accretions are removed from the tooth surface by the active abrasive area of said ultrasonic tip, said safe nonabrasive area that surrounds said active abrasive area prevents abrasion of the tooth surface even while the working area of said ultrasonic tip engages the surfaces of the tooth.

15. The method of claim 12, further including the step of removing at least a portion of accretions of material from a tooth root in a location not visible by a user of the ultrasonic tip, and without damaging portions of the tooth surface.

16. The method of claim 12, further including the step of engaging the ultrasonic tip with the tooth surface to reduce the roughness of accretions therefrom without concern of removing portions of the tooth surface.

17. The method of claim 14, further including removing portions of the accretions of the tooth surface without rotation of said ultrasonic tip.

18. The method of claim 14, further including reducing the height of the accretions until the abraded tooth surface is substantially smooth.

19. A tool for reducing a roughness of accretions from a tooth surface, said accretions defined by raised portions on the tooth surface, said tool comprising:
   an elongated tip formed of a rigid metal and of a size suitable for ultrasonic vibrations;
   said elongate tip having a working area that includes a smooth surface and a depression formed in the smooth surface, the smooth surface of said working area is not effective to damage the tooth surface;
   the depression of said working area being formed in said smooth surface so that the smooth surface surrounds said depression; and
   an abrasive mechanism located in said depression and responsive to the ultrasonic vibrations of said tool to reduce the roughness of the raised portions of the accretions that project into said depression, wherein after the roughness of the raised portions of the accretions is reduced by the abrasive mechanism of said working area, the smooth surface that surrounds said depression engages the tooth surface and prevents further abrasion of the tooth surface, even while the working area of said tool engages the surface of the tooth.

20. The tool of claim 19, wherein said abrasive mechanism comprises a grit bonded to a surface of said depression.

21. The tool of claim 19, wherein said abrasive mechanism comprises a sharp edge formed in said depression.

22. The tool of claim 19, wherein said tool is structured to reduce the roughness of the raised portions of the accretions without rotation of said tool.

23. The tool of claim 19, wherein the depression is constructed with a depth such that the abrasive mechanism causes substantially complete removal of said raised portions from the workpiece.

\* \* \* \* \*